(12) United States Patent
Izawa

(10) Patent No.: US 10,285,587 B2
(45) Date of Patent: May 14, 2019

(54) OCULAR FUNDUS IMAGING SYSTEM

(71) Applicant: KOWA COMPANY, LTD., Aichi (JP)

(72) Inventor: Yusuke Izawa, Tokyo (JP)

(73) Assignee: KOWA COMPANY, LTD., Aichi (JP)

( * ) Notice: Subject to any disclaimer, the term of this patent is extended or adjusted under 35 U.S.C. 154(b) by 0 days.

(21) Appl. No.: 15/551,973

(22) PCT Filed: Feb. 25, 2016

(86) PCT No.: PCT/JP2016/055562
§ 371 (c)(1),
(2) Date: Aug. 18, 2017

(87) PCT Pub. No.: WO2016/136859
PCT Pub. Date: Sep. 1, 2016

(65) Prior Publication Data
US 2018/0064334 A1 Mar. 8, 2018

(30) Foreign Application Priority Data
Feb. 27, 2015 (JP) ................. 2015-038341

(51) Int. Cl.
*A61B 3/14* (2006.01)
*A61B 3/12* (2006.01)
*A61B 3/15* (2006.01)
*A61B 3/00* (2006.01)

(52) U.S. Cl.
CPC .............. *A61B 3/12* (2013.01); *A61B 3/0008* (2013.01); *A61B 3/14* (2013.01); *A61B 3/15* (2013.01); *A61B 3/152* (2013.01); *A61B 3/0041* (2013.01); *A61B 3/0091* (2013.01); *A61B 3/158* (2013.01)

(58) Field of Classification Search
CPC .. A61B 3/14; A61B 3/102; A61B 3/12; A61B 3/0041; A61B 3/15
USPC .......... 351/206, 208, 213, 221, 246
See application file for complete search history.

(56) References Cited

U.S. PATENT DOCUMENTS

2014/0002795 A1* 1/2014 Yoshino .................. A61B 3/12
351/206

FOREIGN PATENT DOCUMENTS

JP 2014226371 12/2014

\* cited by examiner

*Primary Examiner* — Hung X Dang
(74) *Attorney, Agent, or Firm* — Duane Morris LLP

(57) ABSTRACT

[Problem] To allow imaging light to be appropriately received by a second camera in the case where a first imaging mode (color imaging mode) is changed to a second imaging mode (autofluorescence imaging mode). [Solution] In the first imaging mode, using a dichroic mirror 30 allows light LB to be received by both a first camera C1 and a second camera C2. In the second imaging mode, using a transparent glass 31 allows light LB to be received by the second camera C2. With this configuration, both in the first imaging mode and in the second imaging mode, light LB from an ocular fundus is appropriately received by the second camera C2 whereby an appropriate ocular fundus image can be taken.

5 Claims, 4 Drawing Sheets

OCULAR FUNDUS IMAGING SYSTEM

TECHNICAL FIELD

This invention relates to an ocular fundus imaging system that is configured to take a fundus of a subject eye with two or more cameras.

BACKGROUND ART

Various configurations of ocular fundus imaging systems to watch eyes of subjects and/or take images thereof have been proposed, and such systems for carrying out both imaging modes, color imaging and autofluorescence imaging (FAF imaging) have been also proposed (see patent related document 1).

FIG. 4(a) is a block diagram that shows an instance of a configuration of a conventional ocular fundus imaging system wherein a reference C1 denotes a first camera for color imaging, a reference number C2 denotes a second camera for carrying out an alignment at the time of the color imaging and the autofluorescence imaging, and a reference number 30 denotes a dichroic mirror for guiding a light LB from the fundus of the subject's fundus (not shown) to the first camera C1 and the second camera C2 so as to be divided. In the autofluorescence imaging with the second camera C2 in such a configuration, the dichroic mirror 30 is moved outside an optical path (see an arrow Q of FIG. 4(b)), and the light LB is received by the second camera C2 without dividing the light.

PRIOR ART

Patent-Related Document

[Patent-related document 1]: Japanese Patent Application Publication No. 2014-226371

DISCLOSURE OF INVENTION

Problems to be Solved by Invention

If the dichroic mirror 30 is moved outside the optical path, but, the optical path of the light LB is shifted from an optical axis R of the second camera C2 (see a reference number δ of FIG. 4(b), and it is not possible to obtain a proper image.

The object of the invention is to provide an ocular fundus imaging system for solving the above-mentioned problems.

Means for Solving Problems

A first aspect of the invention exemplarily shown in FIG. 1 is an ocular fundus imaging system (1), comprising:

an illuminator (2) that irradiates light to a fundus of a subject eye (E);

an optical path divider (30) that is configured to be freely moved, and that divides a reflected light (LB) that is reflected from the fundus by irradiating the light through the illuminator (2) into two optical paths (PB1, PB2) ("the first optical path" and "the second optical path" hereinafter) when being located in an optical path of the reflected light (LB) (see a reference number PB, "the reflected optical path" hereinafter);

an optical path corrector (31) that is configured to be freely moved and that guides the reflected light (LB) to the second optical path (PB2) when being located in the reflected optical path (PB);

a first camera attaching section (4) that attaches a first camera (C1) at a position where the reflected light (LB) that passes through the first optical path (PB1) is able to be received;

a second camera (C2) that is located at a position where the reflected light (LB) that passes through the second optical path (PB2) is able to be received;

a reflected optical path switcher (32) that movably supports the optical path divider (30) and the optical path corrector (31) and switches the optical path in such a way that one of the optical path divider (30) and the optical path corrector (31) is selectively located in the reflected optical path (PB) and the other is located outside the reflected optical path (LB);

a first filter (F1) that transmits light in a first wavelength range;

a first filter moving section (G1) that movably supports the first filter (F1) to a position in an optical path between the illuminator (2) and the fundus (see a reference number PA, "the illumination path" hereinafter) ("the first filter insertion position" hereinafter) or a position outside the illumination path ("the first filter extraction position" hereinafter);

a second filter (F2) that transmits light in a second wavelength range;

a second filter moving section (G2) that movably supports the second filter (F2) to an upstream position rather than a position in the reflected optical path (PB) where the optical path corrector (31) is located ("the second filter insertion position" hereinafter) or a position outside the reflected optical path ("the second filter extraction position" hereinafter); and an imaging mode switcher (5) that switches a first imaging mode wherein the first filter (F1) is moved to the first filter extraction position by driving the first filter moving section (G1), the second filter (F2) is moved to the second filter extraction position by driving the second filter moving section (G2), and the optical path divider (30) is located in the reflected optical path (PB) and the optical path corrector (31) is located outside the reflected optical path by driving the reflected optical path switcher (32) or a second imaging mode wherein the first filter (F1) is moved to the first filter insertion position by driving the first filter moving section (G1), the second filter (F2) is moved to the second filter insertion position by driving the second filter moving section (G2), and the optical path divider (30) is located outside the reflected optical path and the optical path corrector (31) is located in the reflected optical path (PB) by driving the reflected optical path switcher (32).

A second aspect of the invention is the ocular fundus imaging system (1), wherein the second camera (C2) is configured so as to take still images and moving images, and it is possible to take moving images when watching the fundus with the second camera (C2) in the first imaging mode and the second imaging mode.

A third aspect of the invention is the ocular fundus imaging system (1), further comprising an amplifier (90) that amplifies image signals outputted from imaging element (C2a) in the second camera (C2), and a gain adjuster (91) that adjusts the gain of the amplifier (90) in the case of watching the fundus with the second camera (C2) in the first imaging mode, the case of watching the fundus with the second camera (C2) in the second imaging mode, and in the case of imaging the fundus with the second camera (C2) in the second imaging mode.

A fourth aspect of the invention is the ocular fundus imaging system (1), wherein the first filter (F1) is an exciter filter which can pass the light in the wavelength range 500 nm to 600 nm, and the second filter (F2) is a barrier filter which can pass the light in the wavelength range 640 nm to 740 nm.

A fifth aspect of the invention is the ocular fundus imaging system (1), wherein the optical path divider (30) is a dichroic mirror which reflectance of the light in the wavelength range 450 nm through 650 nm is 98% or more and transmissivity of the light in the wavelength range 800 nm through 950 nm is 90%, and the optical path corrector (31) is a glass which transmissivity in the wavelength range 630 nm through 950 nm is 98% or so.

The number in parentheses shows the corresponding element in the drawings for the sake of convenience, accordingly, the descriptions are not restricted and bound by the descriptions on the drawings.

Effects of Invention

According to the $1^{st}$, $2^{nd}$, $4^{th}$ and $5^{th}$ aspects of the invention, in the first imaging mode, the reflected light is divided through the optical path divider so that both the first and second cameras can receive light. In such a configuration, it is possible to properly image the fundus (preferably, the color imaging) with the first camera while watching the fundus with the second camera. And, in the second imaging mode, the first camera receives the reflected light, so that it is possible to carry out the autofluorescence imaging by using the suitable filters as the first and second filters. Furthermore, when carrying out the second imaging mode, the optical path corrector is located so as to guide the reflected light to the second camera, so that it is possible to obtain the proper fundus image without generating a shift between the optical axis of the second camera and the reflected light.

According to the $3^{rd}$ aspect of the invention, it is possible to obtain uniform images with proper brightness in all imaging cases.

BRIEF DESCRIPTION OF DRAWINGS

FIG. 3(b) is a side view of FIG. 3(a), and FIG. 3(c) is a front view that shows an example of a shape of a ring slit.

PREFERRED EMBODIMENT

Embodiments of the invention are now explained, referring to appended FIGS. 1 through 4.

Figure 1:
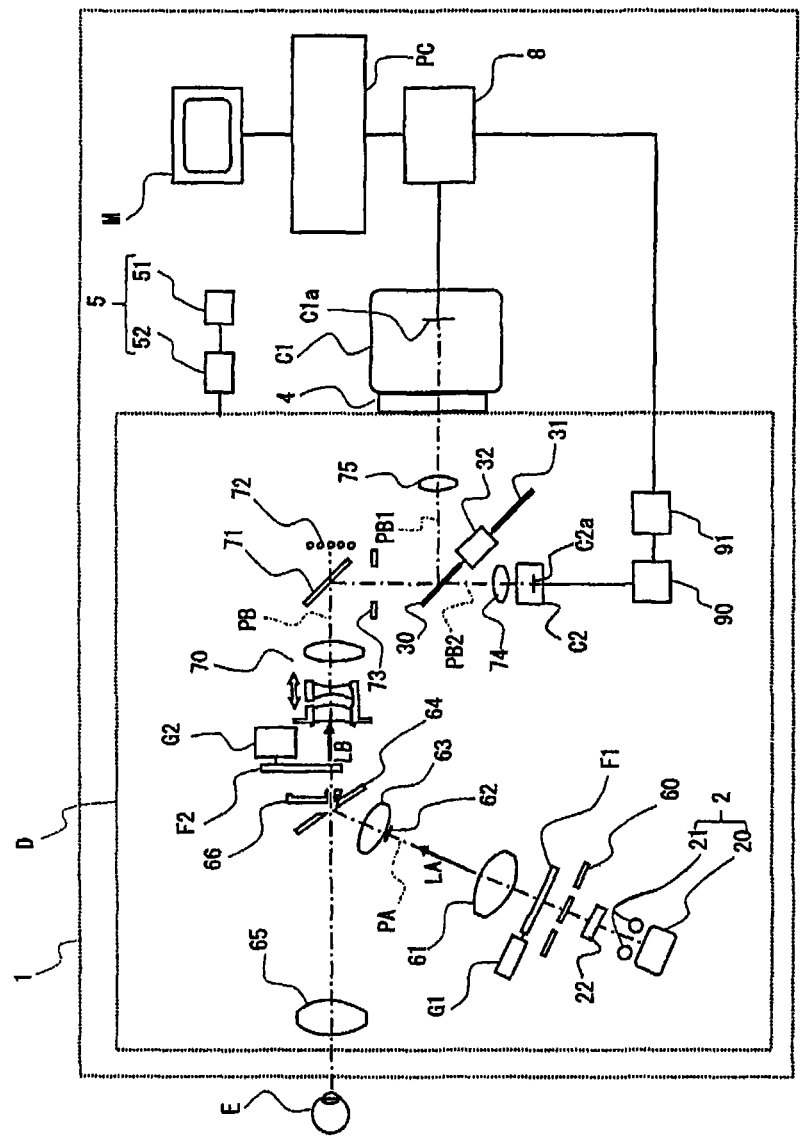
FIG. 1 is a block diagram that shows an example of a structure of an ocular fundus imaging system according to the invention.

An ocular fundus imaging system according to the invention is exemplarily shown with a reference number 1 in FIG. 1, and has at least the followings.

an illuminator 2 that irradiates illumination light LA to a fundus of a subject eye E an optical path divider 30 that is configured to be freely moved, and that divides a reflected light LB that is reflected from the fundus by irradiating the illumination light through the illuminator 2 into two optical paths PB1, PB2 ("the first optical path" and "the second optical path" hereinafter) when being located in an optical path PB of the reflected light LB ("the reflected optical path" hereinafter)

an optical path corrector 31 that is configured to be freely moved and that guides the reflected light LB to the second optical path PB2 when being located in the reflected optical path PB a first camera attaching section 4 that attaches a first camera C1 at a position where the reflected light LB that passes through the first optical path PB1 is able to be received a second camera C2 that is located at a position where the reflected light LB that passes through the second optical path PB2 is able to be received a reflected optical path switcher 32 that movably supports the optical path divider 30 and the optical path corrector 31 and switches the optical path in such a way that one of the optical path divider 30 and the optical path corrector 31 is selectively located in the reflected optical path PB and the other is located outside the reflected optical path a first filter F1 that transmits light in a first wavelength range a first filter moving section G1 that movably supports the first filter F1 to a position in an optical path PA between the illuminator 2 and the fundus ("the illumination path" hereinafter) ("the first insertion position" hereinafter) or a position outside the illumination path ("the first filter extraction position" hereinafter)

a second filter F2 that transmits light in a second wavelength range a second filter moving section G2 that movably supports the second filter F2 to an upstream position rather than a position in the reflected optical path PB where the optical path corrector 31 is located (that is, the position in the reflected optical path PB between the fundus and the optical path corrector 31, "the second filter insertion position" hereinafter) or a position outside the reflected optical path (the second filter extraction position" hereinafter)

an imaging mode switcher 5 that switches a first imaging mode wherein the first filter F1 is moved to the first filter extraction position by driving the first filter moving section G1, the second filter F2 is moved to the second filter extraction position by driving the second filter moving section G2, and the optical path divider 30 is located in the reflected optical path PB and the optical path corrector 31 is located outside the reflected optical path by driving the reflected optical path switcher 32 or a second imaging mode wherein the first filter F1 is moved to the first filter insertion position by driving the first filter moving section G1, the second filter F2 is moved to the second filter insertion position by driving the second filter moving section G2, and the optical path divider 30 is located outside the reflected optical path and the optical path corrector 31 is located in the reflected optical path PB by driving the reflected optical path switcher 32.

In the specification, a section shown with a reference number D (that is, the section including the illuminator 2, the filters F1, F2, the filter moving sections G1, G2, the optical path divider 30, the optical path corrector 31, and the reflected optical path switcher 32) is properly referred to as "an ocular fundus imaging device". And, preferably, the ocular fundus imaging system 1 is comprised of the optical fundus imaging device D, the first camera C1 attached to the first camera attaching section 4 of the optical fundus imaging device D. In this case, a data storage (not shown) which is a HDD, a SSD or a storage media, such as a SD card, a USB memory, and a compact flash (registered trademark) may be located in the ocular fundus imaging device D so that images obtained through the first camera C1 or the second camera C2 can be stored therein. And, a personal computer PC (concretely speaking, a desktop personal computer, a note personal computer, a tablet PC or a smartphone) may be connected with the ocular fundus imaging device D through an image transporter 8 by a wireless or wired channel so that images obtained by the first camera C1 or the second camera C2 can be captured into the personal computer PC through the image transporter 8. Furthermore, a monitor M may be connected with the personal computer PC so that images obtained the respective cameras C1, C2 can be displayed on the monitor M.

The illuminator 2 is an observation light source 20 that is a halogen lamp or a LED, or an imaging light source 21 that is a xenon flash lamp or a high brightness LED, for instance. Preferably, a diffusion board 22, a ring slit 60, the first filter F1, lighting optical systems 61, 63, a ring slit 62, and a holed mirror 64 are located, and an objective lens 65 is located at a position opposed to the subject eye E on a side where the light is radiated from both light sources 20, 21 (that is, the downstream side of the illumination path PA). Preferably, an imaging diaphragm 66 is located at a hole section of the holed mirror 64, and a focus lens 70 for focus adjustment through moving the position on the reflected optical path PB, a half mirror 71 and an inside fixation lamp 72 are located on the downstream side of the imaging diaphragm 66.

Figure 2:
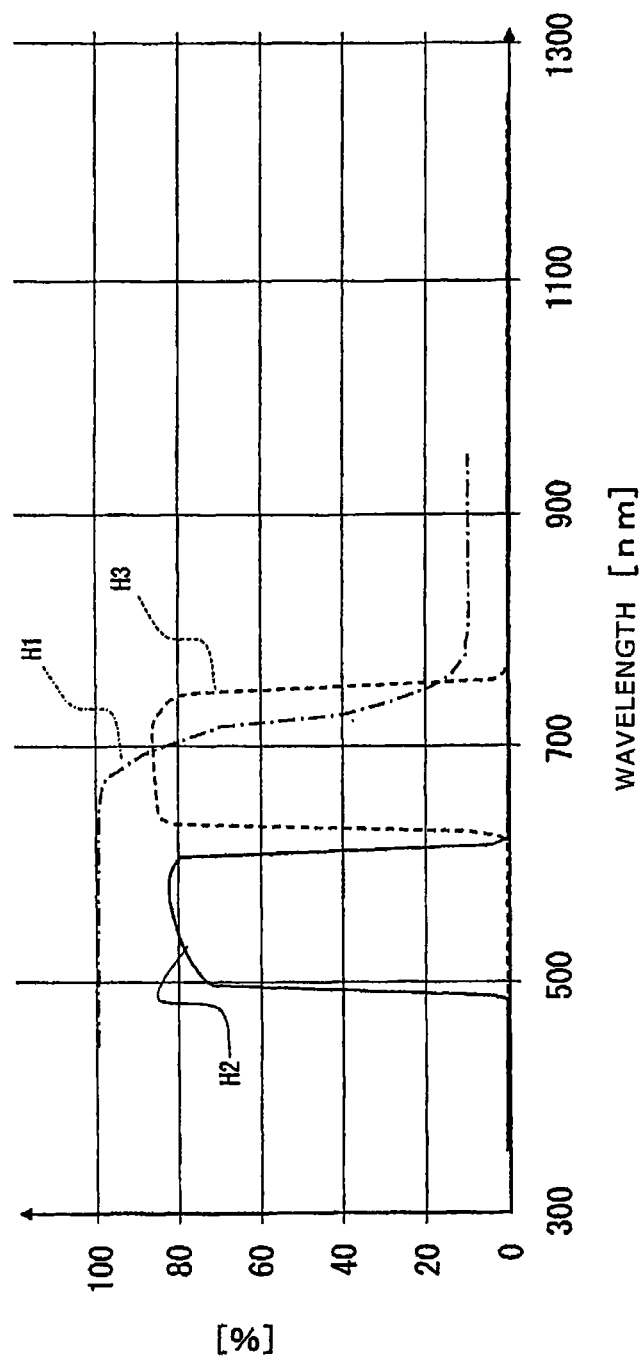
FIG. 2 is a view that shows optical characteristics of an optical path divider, a first filter and a second filter wherein H1 shows a reflectance of the optical path divider, H2 shows a transmissivity of the first filter, and H3 shows a transmissivity of the second filter.
Figure 3:
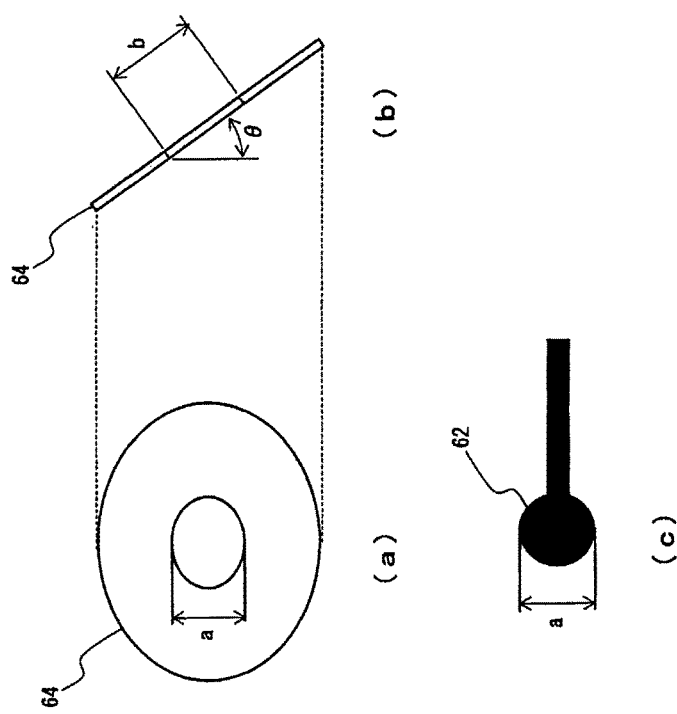
FIG. 3 (a) is a front view that shows an example of a shape of a holed mirror.
Figure 4:
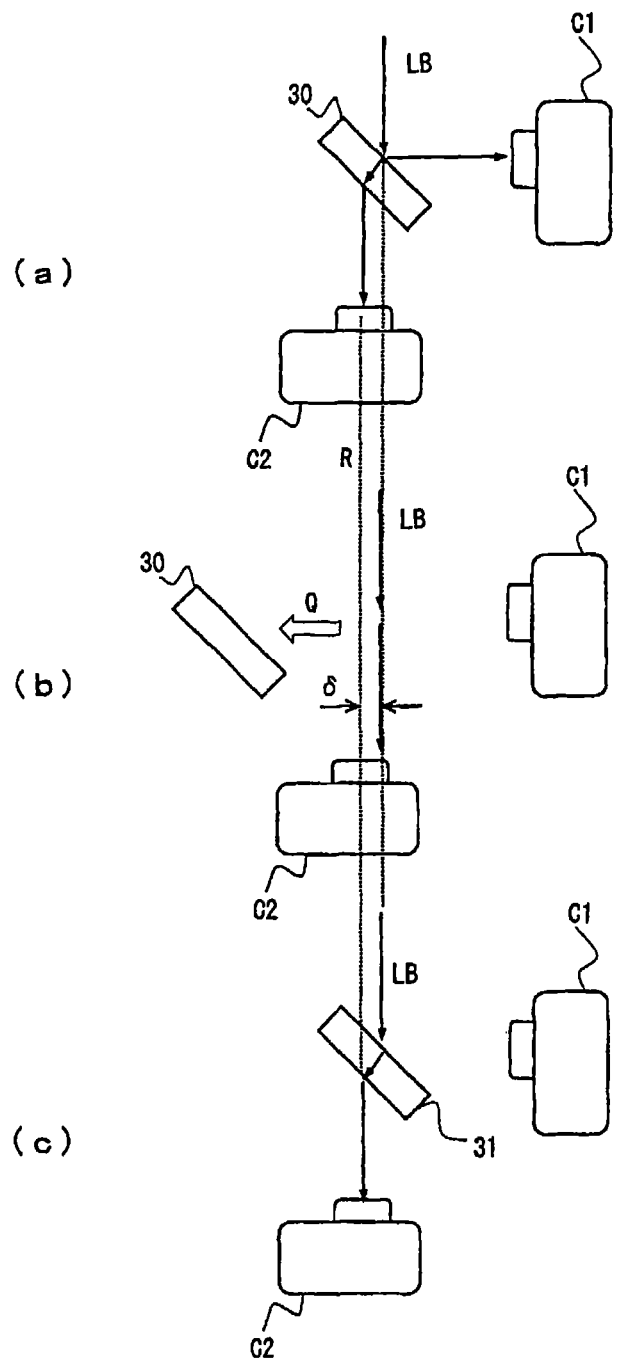
FIG. 4(a), (b) are typical views for explaining conventional problems.
FIG. 4(c) is a typical view for explaining effects of the invention.

On the other hand, the optical path divider 30 is a dichroic mirror (preferably, which reflectance of the light in the wavelength range 450 nm through 650 nm that is used for color imaging is 98% or more and transmissivity of the light in the wavelength range 800 nm through 950 nm that is used at a time of observation before imaging with infrared light is 90%, as exemplarily shown with a reference number H1 in FIG. 2), for instance. The optical path corrector 31 is one that can reduce the amount of the reflected light advancing to the first optical path PB1 in a predetermined wavelength range and can increase the amount of the reflected light advancing to the second optical path PB2, such as a transparent glass which transmissivity is 98% or so in the wavelength range 630 nm through 950 nm that is used for autofluorescence imaging, for instance. In configuration of the invention, the optical path of the reflected light LB that is guided through the optical path corrector 31 almost corresponds with the optical path PB2 of both optical paths PB1, PB2 that are divided through the optical path divider 30. For such a configuration is taken by various kinds of methods, such as a method wherein the shape (the thickness) or the refractive index is almost equal between both the optical path divider 30 and the optical path corrector 31, and the position to be located (the position in the middle of the reflected optical path) or the angle (the posture) is almost equal between both 30, 31 so that the optical path after passing the optical path divider 30 is almost equal to the optical pass passing the optical path corrector 31, and a method wherein the shape and/or the refractive index is not almost equal between both 30 and 31, but the position to be located (the position in the middle of the reflected optical path) or the angle (the posture) is made proper between both so that the optical path after passing the optical path divider 30 is almost equal to the optical path passing the optical path corrector 31.

The reflected optical path switcher 32 are driving motors or various kinds of actuators, for instance.

On the other hand, the first camera C1 is the camera on the market for color imaging, preferably a digital camera capable of imaging in color, for instance, and the second camera C2 is a monochrome camera capable of autofluorescence imaging and observing and imaging with infrared light, for instance, and preferably, is capable of obtaining moving images as well as still images. Besides, the second camera C2 may be detachably attached to the ocular fundus imaging device D, similar to the first camera C1.

Furthermore, the first filter F1 is an exciter filter which first wavelength range is 500 nm to 600 nm (that is, the exciter filter which can pass the light in the wavelength range 500 nm to 600 nm) (see H2 of FIG. 2), for instance, and the second filter F2 is a barrier filter which second wavelength range is 640 nm to 740 nm (that is, the barrier filter which can pass the light in the wavelength range of 640 nm to 740 nm) (see H3 of FIG. 2), for instance. Besides, the first and second filter moving sections G1, G2 are driving motors, and various kinds of actuators, for instance.

In the first imaging mode, the first and second filters F1, F2 are retracted at the positions outside the optical path, that is, at the first and second extraction positions, and the reflected light LB is divided into the first optical path PB1 and the second optical path PB2 through the optical path divider 30. For this reason, it is possible to image in color with the first camera C1 after carrying out alignment with the second camera C2. At this time, preferably, the light is ejected from the imaging light source 21 by pushing down a shutter of the first camera C1. In the second imaging mode, the reflected light LB advances to the second optical path PB2. Then, the alignment and the imaging are done through the second camera C2. Preferably, the first filter F1 and the second filter F2 are inserted into the optical path at the same time of the imaging, that is, when a shutter button is pushed down so that the filters F1, F2 are inserted, and thereafter, a flash lamp (that is, the imaging light source 21) emits light, and the image is captured through the second camera C2. In a case where the barrier filter which second wavelength range is 640 nm to 740 nm is used as the second filter F2, and the transparent glass which transmissivity in the wavelength range 630 nm to 950 nm is 98% or so is used as the optical path corrector 31, almost all of the reflected light LB is guided to the second camera C2 and bright images can be taken.

Preferably, the imaging mode switcher 5 is comprised of an operation section 51 to be operated by an operator, and a driving controller 52 that sends signals from the operation section 51 to the filter moving sections G1, G2 and the optical path switcher 32 and controls these driving. In FIG. 1, a switch, a button, a touch panel or the like is located on a side of the ocular fundus imaging device D as the operation section 51 of the imaging mode switcher 51, and a dedicated circuit board is provided on the side of the ocular fundus imaging device D as the driving controller 52 of the imaging mode switcher 5. But, alternatively, a dedicated application software is installed into the personal computer PC so as to function as the driving controller 52, and a keyboard or a mouse that is connected with the personal computer PC may function as the operation section 51. The other operations (that is, various kinds of operations necessary for taking the fundus images) may be put in a similar state. The operation section and the controller that are necessary for the operations may be provided on the side of the personal computer PC, or on the side of the ocular fundus imaging device D.

According to the invention, in the first imaging mode, the reflected light LB is divided through the optical path divider 30 so that both the first and second cameras C1, C2 can receive light (see FIG. 4(a)). So, it is possible to properly image the fundus (preferably, the color imaging) with the first camera C1 while watching the fundus with the second camera C2. And, in the second imaging mode, the first camera C1 receives the reflected light LB, so that it is possible to carry out the autofluorescence imaging by using the suitable filters as the first and second filters F1, F2.

If the optical path divider 30 is only moved outside the optical path when changing the first imaging mode (color imaging mode) into the second imaging mode (autofluorescence imaging mode), the optical path of the reflected light LB is shifted from an optical axis R of the second camera C2, as shown in FIG. 4(b). But, according to the invention, the optical path corrector 31 is located so as to guide the reflected light LB to the second camera C2, so that it is possible to take the proper fundus image without generating such a shift.

Preferably, the switching into the optical path divider 30 or the optical path corrector 31 is not done at the same time of the shutter operation, but at the same time of the switching of the imaging mode.

When the second camera C2 is configured so as to take still images and moving images, it is possible to take moving images when watching the fundus with the second camera C2 in the first and second imaging modes. As the result, it is possible to take moving images with the second camera C2 when watching in the first imaging mode (1), to take moving images with the second camera C2 when watching in the second imaging mode (2), and to take still images with the second camera C2 in the second imaging mode (3). But, the optical path divider 30 is used in the first imaging mode although the optical path corrector 31 is used in the second imaging mode and the filters F1, F2 are used at the time of taking images when imaging in the second imaging mode, so that the amount of light that the second camera C2 receives is different. Then, preferably, an amplifier 90 that amplifies image signals outputted from the second camera C2 (concretely speaking, from imaging element thereof C2a), and a gain adjuster 91 that adjusts the gain of the amplifier 90 so that the brightness of the fundus image becomes substantially constant in the case of watching the fundus with the second camera C2 in the first imaging mode, the case of watching the fundus with the second camera C2 in the second imaging mode, and the case of imaging the fundus with the second camera C2 in the second imaging mode. By doing so, it is possible to obtain uniform images with proper brightness in all cases (1) to (3). Preferably, the gain of the first camera C1 (an imaging element C1a) in the first imaging mode is adjusted as well as the gain of the second camera C2. The gain adjuster 91 may be provided inside a main body (that is, the inside of the ocular fundus imaging device D) as exemplarily shown in FIG. 1, or may be provided so as to connect the outside of the main body (that is, the outside of the ocular fundus imaging device D), or a dedicated application software may be installed in the personal computer PC so that the personal computer PC functions as the amplifier 90 or the gain adjuster 91.

An instance for determining size of the gain is now mentioned. When comparing the case (1) (that is, the case of taking moving images with the second camera C2 when watching in the first imaging mode) and the case (2) (that is, the case of taking moving images with the second camera C2 when watching in the second imaging mode) with each other, the amount of light in the case (1) is smaller than one in the case of (2) under an influence of the dichroic mirror. Then, the gain in the case (1) is made bigger than one in the case (2). On the other hand, in the case (3) (that is, the case of taking the still images with the second camera C2 in the second imaging mode), preferably, the gain is set bigger for a purpose of reducing a burden on the subject by taking the images with the smaller amount of light as much as possible. On the contrary, the gain may be smaller for reducing noise of the image and the amount of light for taking images may be increased for the purpose of obtaining high quality images. For these reasons, it is convenient if the examiner is able to optionally set the gain and the amount of the light for taking images, and is also able to select one of combinations of the gain and the amount of such a light that are often used.

Preferably, the fundus is observed over a relatively wide range when watching the fundus image. Preferably, on the other hand, it is desired that an edge of the fundus image (the peripheral portion) is removed at the time of taking images so that a flare does not appear in the image since the flare is easy to appear on the edge of the fundus image. One method to do so is to locate a visual field mask 73 made of metal or the like on the downstream side of the optical path of the half mirror 71 (the lower side of the figure) so as to remove the flare. But, a considerably low-resolution camera is often used as the second camera C2 for autofluorescence imaging since in such a camera, being highly sensitive has a higher priority, so that the edge portion of the visual field mask 73 that is cut off in the shape of a circle is not a perfect circle but a zigzag line, and is not good looking. Then, preferably, an electronic mask is automatically used for the still image taken through the second camera C2 so that the bounds of the image obtained is made narrower than the observation bounds in order to remove the flare.

Preferably, a diaphragm is unified with the second filter F2. In such a case, it is possible to simultaneously adjust the amount of light for taking images (the reflected light) (change the diaphragm diameter) in the second imaging mode (autofluorescence imaging).

In a case of the non-mydriasis autofluorescence imaging, the light may not sufficiently reach the fundus from the illuminator 2, depending on the miosis state of the subject and for this reason, the image may be dark. As a countermeasure, if a diameter of the hole of the holed mirror 64 is b and an inclined angle is θ as shown in FIG. 3(b), an diameter a (see FIG. 3(c)) of the ring slit 62 may be a=b·cos θ. By doing so, it is possible to increase the amount of the light that reaches the fundus as much as possible so as to brighten the obtained image. The size of the ring slit 62 is a proper one with no unnecessary flare, taking the inclined angle of the holed mirror 64 into consideration. But, in many cases, the ring slit 62 having rather bigger size is actually designed in consideration of the problem of the light circumstance and the balance of various kinds of elements. When effectively using the amount of the light in this way, the ocular fundus imaging device can be suppressed from being increased in size and weight and heating quantity since it is not necessary to use the big-sized illuminator with much quantity of ejection light.

EXPLANATION OF REFERENCE NUMBERS

4 . . . first camera attaching section
5 . . . imaging mode switcher
30 . . . optical path divider
31 . . . optical path corrector 32 . . . reflected optical path switcher
90 . . . amplifier
91 . . . gain adjuster
C1 . . . first camera
C2 . . . second camera
F1 . . . first filter
F2 . . . second filter
G1 . . . first filter moving section
G2 . . . second filter moving section
LB . . . reflected light
PA . . . optical path
PB . . . reflected optical path
PB1 . . . first optical path
PB2 . . . second optical path

The invention claimed is:

1. An ocular fundus imaging system, comprising:

an illuminator that irradiates light to a fundus of a subject eye;

an optical path divider that is configured to be freely moved, and that divides a reflected light that is reflected from the fundus into a first optical path and a second optical path by irradiating the light through the illuminator when positioned in an optical path of the reflected light, the reflected optical path;

an optical path corrector that is configured to be freely moved and that guides the reflected light to the second optical path when positioned in the reflected optical path;

a first camera attaching section that attaches a first camera at a position where the reflected light that passes through the first optical path can be received;

a second camera that is located where the reflected light that passes through the second optical path can be received;

a reflected optical path switcher that movably supports the optical path divider and the optical path corrector and switches the optical path in such a way that one of the optical path divider and the optical path corrector is selectively located in the reflected optical path and the other is located outside the reflected optical path;

a first filter that transmits light in a first wavelength range;

a first filter moving section that movably supports the first filter to a first filter insertion position which is a position in an optical path between the illuminator and the fundus or to a first filter extraction position which is a position outside the optical path between the illuminator and the fundus;

a second filter that transmits light in a second wavelength range;

a second filter moving section that movably supports the second filter to a second filter insertion position which is a position in the reflected optical path that is upstream from where the optical path corrector is located, or to a second filter extraction position which is a position outside the reflected optical path; and an imaging mode switcher that switches a first imaging mode wherein the first filter is moved to the first filter extraction position by driving the first filter moving section, the second filter is moved to the second filter extraction position by driving the second filter moving section, and the optical path divider is located in the reflected optical path and the optical path corrector is located outside the reflected optical path by driving the reflected optical path switcher or a second imaging mode wherein the first filter is moved to the first filter insertion position by driving the first filter moving section, the second filter is moved to the second filter insertion position by driving the second filter moving section, and the optical path divider is located outside the reflected optical path and the optical path corrector is located in the reflected optical path by driving the reflected optical path switcher.

2. The ocular fundus imaging system according to claim 1, wherein the second camera is configured so as to take still images and moving images, and it is possible to take moving images when watching the fundus with the second camera in the first imaging mode and the second imaging mode.

3. The ocular fundus imaging system according to claim 2, further comprising an amplifier that amplifies image signals outputted from imaging element in the second camera, and a gain adjuster that adjusts the gain of the amplifier in the case of watching the fundus with the second camera in the first imaging mode, in the case of watching the fundus with the second camera in the second imaging mode, and in the case of imaging the fundus with the second camera in the second imaging mode.

4. The ocular fundus imaging system according to claim 1, wherein the first filter is an exciter filter which can pass the light in the wavelength range 500 nm to 600 nm, and the second filter is a barrier filter which can pass the light in the wavelength range 640 nm to 740 nm.

5. The ocular fundus imaging system according to claim 4, wherein the optical path divider is a dichroic mirror whose reflectance of the light in the wavelength range 450 nm through 650 nm is 98% or more and transmissivity of the light in the wavelength range 800 nm through 950 nm is 90%, and the optical path corrector is a glass whose transmissivity in the wavelength range 630 nm through 950 nm is 98% or so.

* * * * *